(12) United States Patent
McBride et al.

(10) Patent No.: US 7,099,801 B1
(45) Date of Patent: Aug. 29, 2006

(54) MEDICAL TESTING INTERNET SERVER SYSTEM AND METHOD

(75) Inventors: George McBride, Cave Creek, AZ (US); Robert Royce, Mesa, AZ (US)

(73) Assignee: CardioBeat.Com, Scottsdale, AZ (US)

( * ) Notice: Subject to any disclaimer, the term of this patent is extended or adjusted under 35 U.S.C. 154(b) by 0 days.

(21) Appl. No.: 09/535,185

(22) Filed: Mar. 27, 2000

(51) Int. Cl.
*G06F 15/00* (2006.01)

(52) U.S. Cl. .................. 702/188; 709/219; 600/300
(58) Field of Classification Search ............... 600/300; 705/2, 5; 340/573.1; 702/188; 709/219
See application file for complete search history.

(56) References Cited

U.S. PATENT DOCUMENTS

| | | | | |
|---|---|---|---|---|
| 5,235,510 A | * | 8/1993 | Yamada et al. | 600/300 |
| 5,339,821 A | * | 8/1994 | Fujimoto | 600/513 |
| 5,416,695 A | * | 5/1995 | Stutman et al. | 364/413.02 |
| 5,704,366 A | * | 1/1998 | Tacklind et al. | 128/716 |
| 5,715,823 A | * | 2/1998 | Wood et al. | 128/660.01 |
| 5,810,747 A | * | 9/1998 | Brudny et al. | 600/595 |
| 5,832,448 A | * | 11/1998 | Brown | 705/2 |
| 5,997,476 A | * | 12/1999 | Brown | 600/300 |
| 6,131,090 A | * | 10/2000 | Basso et al. | 706/23 |
| 6,149,585 A | * | 11/2000 | Gray | 600/300 |
| 6,270,457 B1 | * | 8/2001 | Bardy | 600/300 |
| 6,272,469 B1 | * | 8/2001 | Koritzinsky et al. | 705/2 |
| 6,278,999 B1 | * | 8/2001 | Knapp | 707/9 |
| 6,280,380 B1 | * | 8/2001 | Bardy | 600/300 |
| 6,302,844 B1 | * | 10/2001 | Walker et al. | 600/300 |
| 6,336,900 B1 | * | 1/2002 | Alleckson et al. | 600/485 |
| 6,350,237 B1 | * | 2/2002 | Pelletier et al. | 600/300 |
| 6,440,067 B1 | * | 8/2002 | De Luca et al. | 600/300 |
| 6,502,124 B1 | * | 12/2002 | Shimakawa et al. | 709/203 |
| 6,578,167 B1 | * | 6/2003 | Boorom et al. | 714/727 |
| 6,602,469 B1 | * | 8/2003 | Maus et al. | 422/68.1 |

FOREIGN PATENT DOCUMENTS

| | | | |
|---|---|---|---|
| JP | 174064 | * | 6/1997 |
| JP | 410232766 A | * | 11/1998 |

* cited by examiner

*Primary Examiner*—Marc S. Hoff
*Assistant Examiner*—Paul Kim
(74) *Attorney, Agent, or Firm*—Donalo J. Lenkszus

(57) ABSTRACT

Server apparatus coupled to the Internet is operated to provide medical testing. Medical test measurement data is uploaded to the central server from remote locations via patient Internet apparatus via the Internet. The server selects a computer program algorithm to process said medical test measurement data. The server processes the medical test measurement data in accordance with the selected computer program algorithm to produce test information from said medical test measurement data. The server downloads the test information to predetermined user apparatus coupled to the Internet.

19 Claims, 10 Drawing Sheets

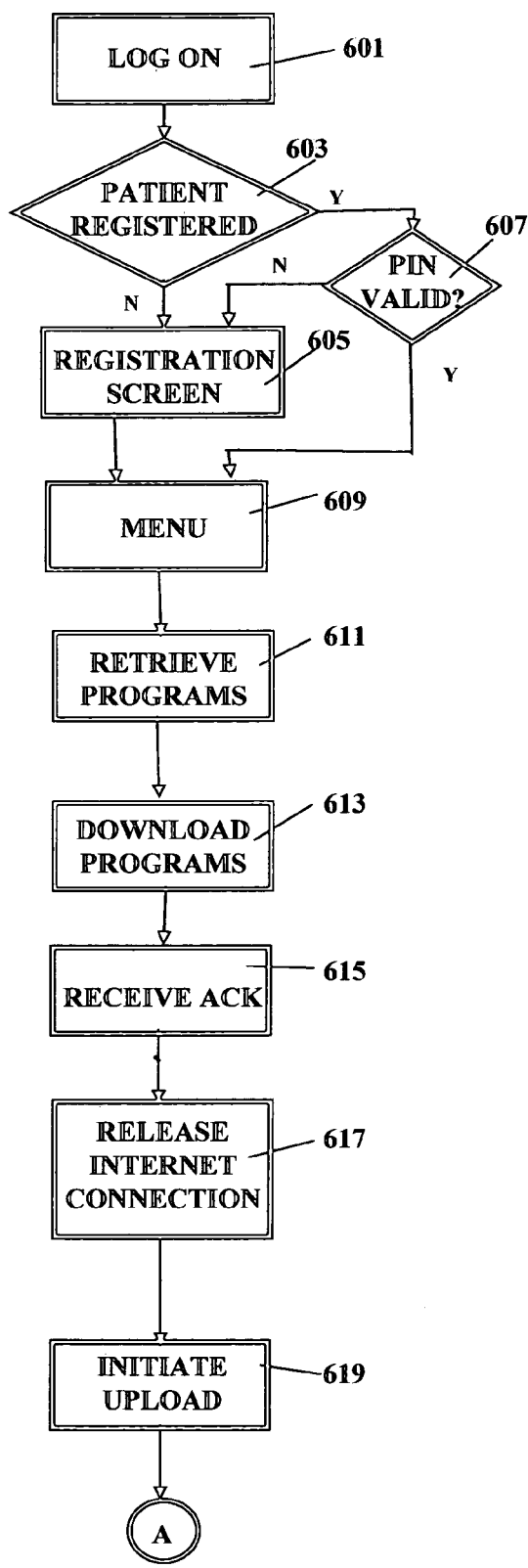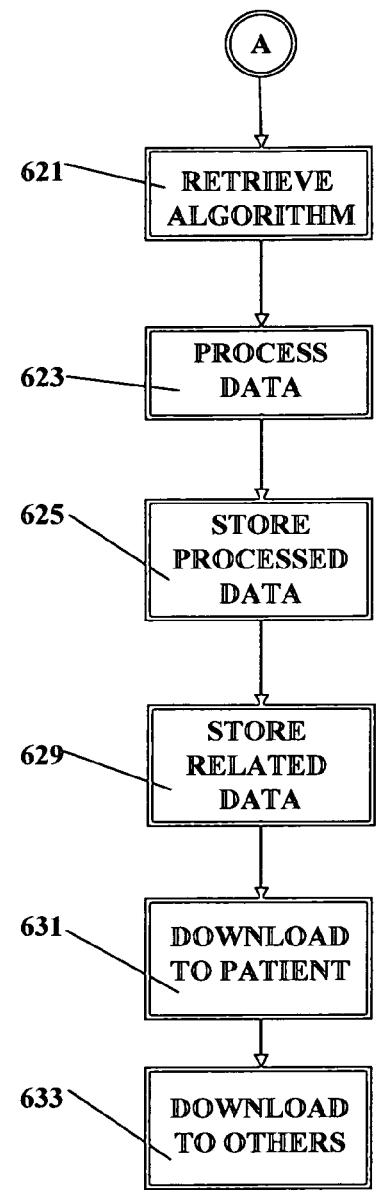
FIG. 6

| FUNCTION | NORMS: | TEST: | DIFF: |
|---|---|---|---|
| SYSTOLIC BLOOD PRESSURE | 120 | 125 | +5 |
| DIASTOLIC BLOOD PRESSURE | 80 | 85 | +5 |
| MEAN BLOOD PRESSURE | 93 | 98 | +5 |
| STROKE VOLUME INDEX | 36.4 | 23.4 | -13 |
| TOTAL SYSTEMIC RESISTANCE | 1247.7 | 1804..6 | +556.9 |
| CARDIAC INDEX | 2.8 | 2.1 | -.7 |
| HEART RATE | 77 | 88 | +11 |
| VASCULAR RIGIDITY | 1.10 | 1.71 | +.61 |
| MEAN SYSTOLIC EJECTION RATE | 131.5 | 62.7 | -68.8 |
| STROKE WORK INDEX | 46.2 | 31.3 | -14.9 |
| LEFT VENTRICULAR EJECTION TIME | .277 | .373 | +.96 |
| PRE-EJECTION PERIOD | .115 | .055 | -.60 |
| PLR = PEP/LVET RATIO | .417 | .146 | -.271 |
| HEATHER INDEX | n/a | 5.9 | n/a |
| DZDT (FIRST DERIVATIVE OF ZO) | 1.93 | .99 | -.94 |
| ZO (TRANSTHORACIC IMPEDANCE) | 25.3 | 25.9 | +.6 |
| STROKE VOLUME | 77.5 | 49.8 | -27.7 |
| CARDIAC OUTPUT | 6.0 | 4.4 | -1.6 |

FIG. 9

Male 55 years old- Jim Smith- Test Date 01-01-2000

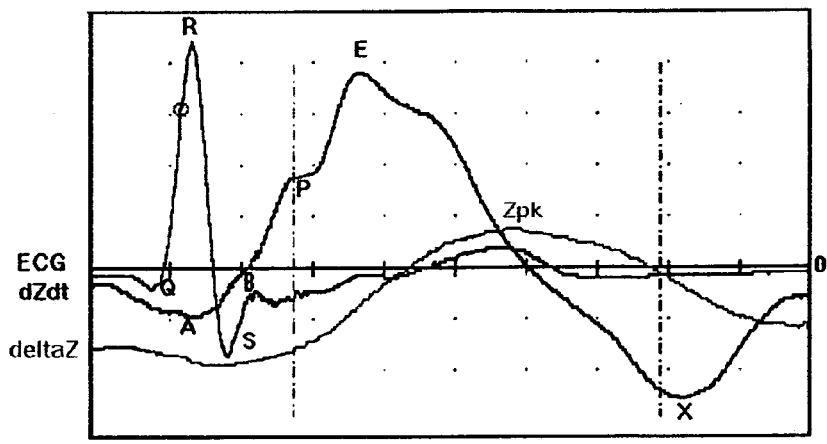

| Major Functions | NORMS | TEST RESULTS | DIFFERENCE |
|---|---|---|---|
| Cardiac Output | 6.0 | 4.4 | -1.6 |
| TSR | 1247.7 | 1804.6 | +556.9 |
| Stroke Volume | 77.5 | 49.8 | -27.7 |

SAMPLE- PERFORMANCE REPORT

Supine L/Zo ratio is normal at 104%. Supine stroke volume index is low
at 23.4 with mildly increased TSR of 1804.6. The heart rate and
blood pressure remain relatively unchanged. These findings indicate
The patient is on the ascending limb of the Starling curve and
no further modification in current therapeutic regimen is necessary
at this time.

FIG. 11

MEDICAL TESTING INTERNET SERVER SYSTEM AND METHOD

FIELD OF THE INVENTION

This invention pertains to medical testing systems, in general, and to a method and system for remote medical testing, in particular.

BACKGROUND OF THE INVENTION

Heart disease is the largest single killer in America killing 960,000 in total, 160,000 between the ages of 35 and 64. More women die from heart disease than men do. The numbers in the industrial world are stunning—58 million Americans and 220 Million Europeans and Asians suffer from heart disease and 5 million Americans and 18 million Europeans have had a heart attack. The cost of heart disease in America is estimated at $286 billion. As the so-called "Baby-Boomers" reach their 60's, it can be expected that the numbers of older people along will cause the cost burden to increase significantly. The number of Americans affected by heart disease is increasing and will continue to increase as the Baby-Boomers join the Senior Citizen's ranks.

The basic method of assessing heart function is thermodilution, a procedure that involves insertion of a catheter into the pulmonary artery. This method is demanding in terms of cost, equipment and skilled personnel time. This is an invasive process requiring direct access to the pulmonary arterial circulation through the neck of groin via a catheter inserted into the vascular system (vena cava) and heart directly into the pulmonary artery.

This procedure can be fatal and cause other complications including pneumothorax, pulmonary artery rupture, arrhythmia, and severe infections. The Journal of the American Medical Association ("JAMA") reported in its September 1996 issue that examined data on 5,735 intensive care patients at five U.S. medical centers revealed that those patients who underwent PAC had a 21% higher risk of death within 30 days compared to those who did not undergo the procedure. This study was underscored by the fact that all patients in both groups of the study were matched for disease severity and prognosis.

Cost is another significant consideration is the use of the catheterization. The mean cost of a hospital stay for critically ill patients having a catheterization is $49,300 (according to the above-referred article in JAMA) as compared to a cost of $35,700 for a critically ill patient who did not undergo the catheterization. The catheterization added $13,600 to the total costs of treating these critically ill patients. The costs to the U.S. healthcare system for each 100,000 catheterizations performed each year is estimated at $200 million for catheters and their insertion, and $1,400 million per year for the complications associated with the procedure.

Impedance cardiography was developed in the 1930's. The NASA space program was first to employ impedance cardiography in the '60's as a non-invasive cardiovascular monitor for astronauts in space. It is used, today, in stand-along devices in medical surroundings. Impedance cardiography is anon-invasive electronic system for measuring impedance changes across the thorax that would be reflective of cardiac function and blood flow from the left ventricle into the aorta.

Impedance cardiography is based upon the principle of a drop in trans-thoracic electrical resistivity that occurs when red blood cells align themselves in a more parallel fashion during ejection of blood into the thoracic-ascending aorta. This phasic drop in trans-thoracic electrical resistivity with each ejection of blood into the aorta is a very small percentage of total trans-thoracic impedance. The signal has both volumetric and velocity contributions to its magnitude and morphology. When high frequency, low energy electricity is passed through tissue, resistance to electrical flow will be lower in wet tissue than in dry tissue. Tissue full of air will have even higher resistivity. The resistance of an electrical conductor is directly proportional to its length and the inherent resistive properties of the conducting material. Resistance is inversely proportional to the mean cross sectional area of the electrical conductor. In other words, a long conductor has more resistance than a short conductor. Thin conductors resist more than thick conductors do. Dry tissue is more resistive than wet tissue. The thorax is an electrical conductor of variable length, volume, and fluid content.

It is possible to safely inject low energy high frequency electrical current through the thorax by placing electrodes on the forehead and distally on the abdomen. One can then measure resistance changes across the thorax. The proximal and distal dimensions of the thorax are defined by encircling electrodes placed at the base of the neck and the lower thorax at the level of the sternal-xiphoid process. It is possible to then measure the resistivity that occurs across a thorax when high frequency constant electrical current is passed between the forehead and abdominal electrode.

The thorax is an electrical conductor that contains several different resistive elements. The lungs contain air and represent a highly resistive component. Skin, subcutaneous fat, and muscle are various thoracic resistive elements, which follow the general principle that the more water, or electrolyte contained per gram of tissue, the lower its resistivity. A third component within the thorax is the heart and great vessels filled with blood, a fluid that may be considered an electrolyte solution with cells added. Blood and salt water are good electrical conductors and therefore have a low resistance. Therefore, the more water in the thorax, the better the conductivity to electrical flow and the lower its resistance. These variations in conductivity can be sensed and reduced to a set of cardiovascular measurements.

Although the need for clinical care is necessary and important, increasingly it is becoming apparent that it is also important to prevent cardiovascular diseases. There is a concurrent need for better management of cardiovascular health.

Even more generally, a need exists for a low cost, system and method for medical testing that expands widespread use of limited medical expertise.

SUMMARY OF THE INVENTION

In accordance with the principles of the invention, a revolutionary health care system is provided. In accordance with the invention, remote medical testing is provided. Internet apparatus is use to receive test data from medical sensors and to upload the test data to a central site via the Internet. At the central site, the test data is processed in accordance with predetermined algorithms to generate test information. The test information may be made available back to the Internet apparatus originating the test data. The test information may also be made available to authorized users via the Internet.

Sever apparatus coupled to the Internet is operated to provide medical testing. Medical test measurement data is uploaded to the central server from remote locations via patient Internet apparatus via the Internet. The server selects a computer program algorithm to process said medical test measurement data. The server processes the medical test measurement data in accordance with the selected computer program algorithm to produce test information from said medical test measurement data. The server downloads the test information to predetermined user apparatus coupled to the Internet.

In accordance with one aspect of the invention, non-invasive impedance cardiography is used in conjunction with Internet access to measure and support management of cardiovascular health. Impedance cardiography is used to gather data from patients. The data is transmitted to a central location via the Internet. At the central location, the data is used to obtain a detailed profile of cardiovascular health. A database is maintained for each patient. The database permits a broad range of service to be provided to the patient. The database is used to provide a medical life history and trend reporting for each patient. Data base storage of test data and personal history provides continuity for precise individual evaluation. Data analysis predicts future health and supports treatment decisions. The sum total of the services is a foundation for lifetime management of cardiovascular health.

BRIEF DESCRIPTION OF THE DRAWING

The invention will be better understood from a reading of the following detailed description in conjunction with drawing figures, in which like reference designations are used to identify like elements, and in which:

FIG. 6 is a flow diagram illustrating operation of the server shown in FIG. 5;

FIG. 9 is a screen display of detailed measurement data;

FIG. 11 is a screen display of information provided to a patient.

DETAILED DESCRIPTION

Figure 1:
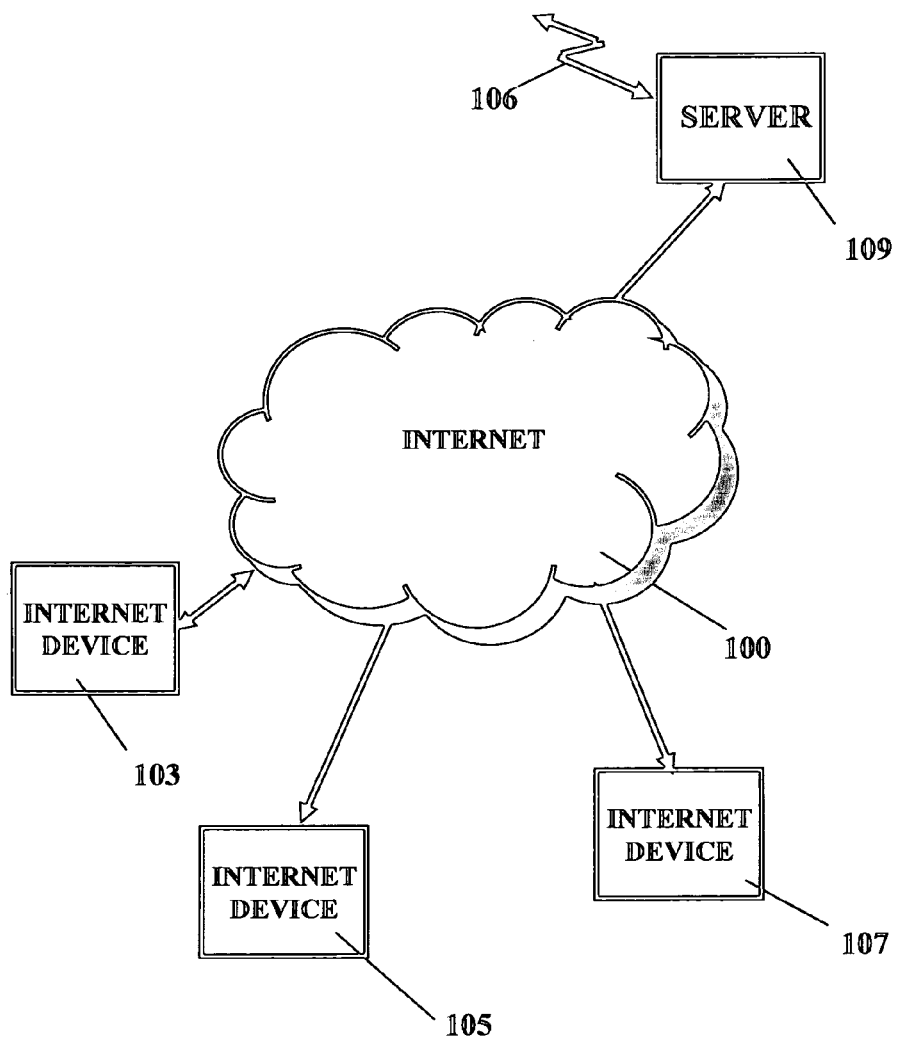
FIG. 1 depicts a system in accordance with the principles of the invention.

Turning now to FIG. 1, the system of the invention is depicted in block diagram form. The system of the invention advantageously utilizes the World Wide Web 100 which is commonly referred to as the Internet. As is conventional in diagrams illustrating utilization of the Internet, the Internet is shown as a cloud in FIG. 1. Particular details of the Internet 100 and Internet connections do not form part of the present invention. Various devices 103, 105, 107, such as personal computers, Internet tablets and the like may access various servers such as server 109. For clarity, all user devices that are connectable to the Internet and that permit a user of the device to download information from the Internet are referred to herein as Internet devices. It will be understood by those skilled in the art that "Internet device" is an inclusive term. The term includes all manner of devices capable of downloading information from the World Wide Web and capable of uploading information to the World Wide Web, and is not in any way intended to limit the type of device that is connectable to the World Wide Web or Internet 100. FIG. 1 further shows a server 109 that is accessible by any of the Internet devices 103, 105, 107 via the Internet 100 and may be accessible by other means also, such as, for example, by telephone line 106. In operation, a user or patient proximate Internet device 103 desires to have test measurements taken. The user or patient may, in accordance with one aspect of the invention desire to perform the test without assistance in some instances, or may have another person assist with the testing. For purposes of clarity, the term "patient" is used to identify the individual from whom test measurement data is being obtained. The patient may or may not be under medical care of a medical practitioner. The system and method of the invention lends itself to both medical diagnostic testing of a type that is necessarily performed under guidance of a medical practitioner and to testing for which the patient may do his or her own testing.

In either case, it is anticipated that the patient will have sensor devices that are utilized to generate measurement data and that are coupleable to an Internet device. The sensor devices may be provided to the patient by any one of a number of methods. In one instance, the patient receives the sensors by delivery after registering with the system of the invention. In other instances, the patient acquires the sensors from a separate source. In still other instances, the sensor devices may for certain tests be available to the patient only by prescription. The sensor devices in the embodiment of the invention in which the patient self tests himself or herself are non-invasive.

To perform a test in accordance with the invention, the patient utilizes an Internet device 103 to access a server 109 coupled to the Internet 100. Internet device 103 logs onto server 109. Server 109 downloads one or more appropriate programs to Internet device 109. In addition, Server 109 downloads instructional information to Internet device 103. The instructional information provides the user of the system step-by-step instructions for setting up and using the test system. The instructional information includes information that instructs the user on how and where to place each sensor and how to connect each sensor to the Internet device 103. In addition, step-by-step instructions are provided in a multimedia format that shows and tells along with text information each step of the test measurement. Testing may take place at nay location where access to a personal computer or other Internet device that is coupleable to the Internet is available. Accordingly, testing in accordance with the invention may be conducted in the home, clinic, or a physician's office. There are no geographic limitations where the testing may occur. Testing may be performed in remote locations as long as there is an Internet device and access to the World Wide Web. Access to the World Wide Web may be via wire or wireless connection. Access may for example be via satellite link or any other access.

In one embodiment of the invention, after appropriate programs and instructional information are downloaded to the Internet device 103, the Internet connection is dropped. Testing is performed off-line from the server 109. Test measurement data is collected by Internet device 103. Upon completion of the testing, Internet device 103 reestablishes a connection to server 109 and uploads the test measurement data to server 109. Server 109 processes the data and downloads the results of processing to Internet device 103 for display to the patient.

Figure 2:
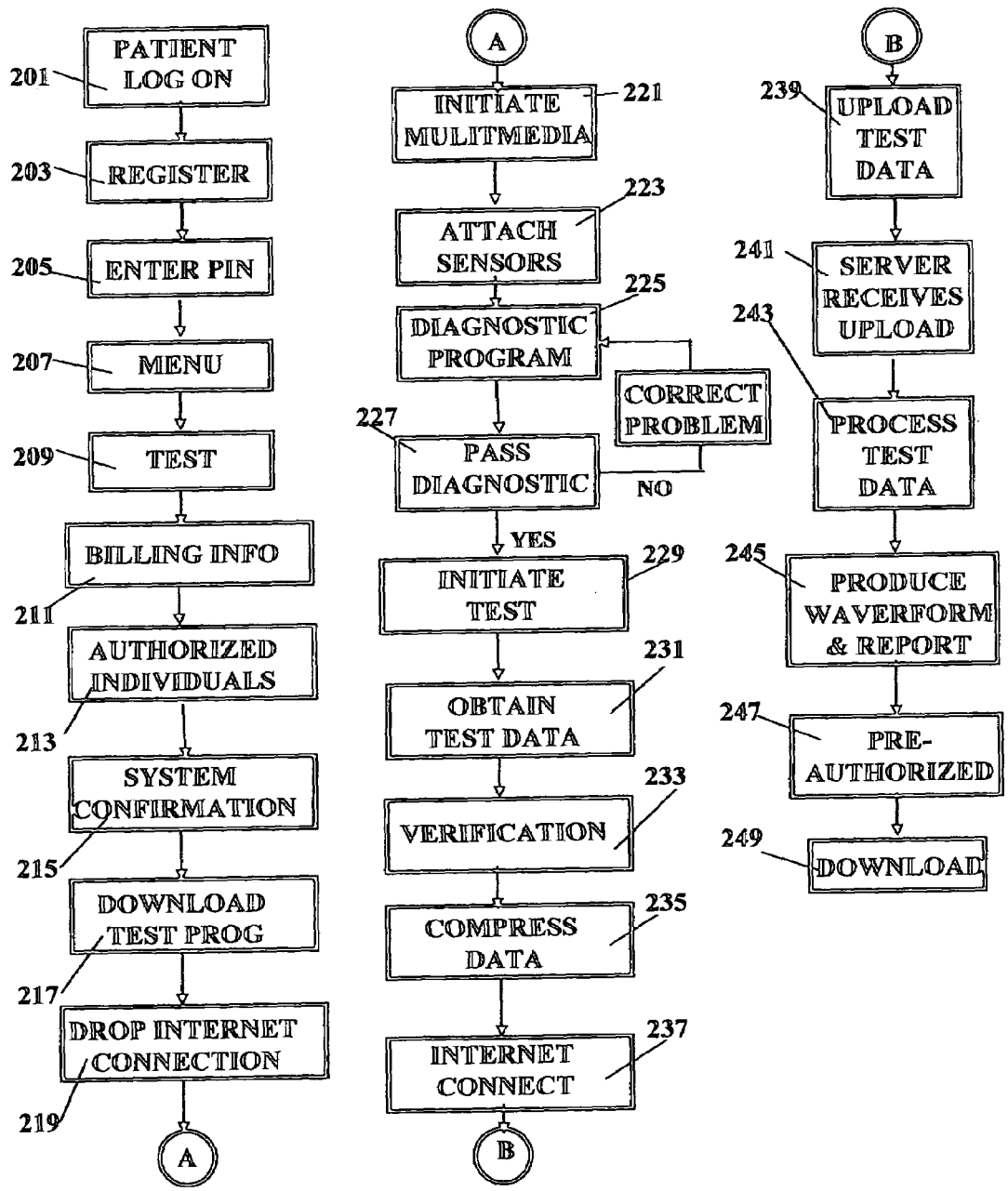
FIG. 2 is a flow diagram illustrating operation of the system of FIG. 1.

Turning now to FIG. 2, operation of the testing method and system from the perspective of the patient will be described. It should be noted that although the operational steps are described in terms of the patient taking action, another person might assist the patient and perform interactive operations on the patient's behalf. At step 201, the patient utilizing Internet device 103 logs onto a web site run by server 109. After logging onto the web site, the patient must identify whether he or she is presently registered with the test system or not at step 203. If the patient has previously registered as a user of the system, the patient has an assigned personal identification number or PIN. At step 205, the patient enters his or her PIN. The patient is then presented with a menu of choices at step 207. If the patient chooses to have a test performed at step 209, the patient will be asked to provide or verify billing or payment information such as providing a credit card number at step 211. The patient is asked to provide information about those individuals he or she will permit to have access to the information at step 213. For example, the patient will indicate one or more medical practitioners to have access to the results of the testing. The system confirms to the patient the test to be performed at step 215. The system at step 217 downloads to the patient's Internet device 103 testing program code for execution of the test. After the program is downloaded, the Internet connection may be dropped at step 219. The downloaded program in the patient's Internet device 103 directs the testing procedure, collects the data from the sensors, conditions the data, and transmits the data to the central system site. Upon completion of the test procedure, the testing program is automatically un-installed.

To perform the test procedure sensors are utilized to obtain measurement data from the patient. Part of the downloaded program to Internet device 103 is a multimedia presentation that steps the patient through the positioning and attachment of the sensor or sensors utilized in the testing. At step 221, the multimedia presentation is initiated. The patient is directed on placement of each sensor and after each sensor is placed, the patient provides an indication that the positioning is complete. After the patient has attached all sensors at step 223 and prior to running a data-collecting test, the testing program at step 225 executes a diagnostic program to check operation and operability of the sensors. If the diagnostic program indicates that the sensors are not operating properly, the program will direct the patient through a routine to correct the problem at step 227. After the diagnostic program indicates that the sensors are operating in an appropriate manner, the testing protocol is initiated at step 229.

After all the test measurement data is obtained at step 231, a verification routine is run at step 233 to determine that the test measurement data appears to be valid data. If the data does not appear to be correct, the patient is instructed to start the process over again. If the program diagnostics are able to pinpoint the problem to a particular sensor, the patient is asked to reattach the suspect sensor. After the program verification routine criteria are satisfied, the test measurement data is compressed and processed for transmission at step 235. The testing program automatically re-establishes an Internet connection to server 109 at step 237.

The test measurement data is uploaded from Internet device 103 to server 109 at step 239 utilizing secure encrypted transmission. The encryption program is part of the downloaded program to Internet device 103 from server 109. Server 109 receives and decodes the encrypted test measurement data at step 241. Server 109 processes the test measurement data in accordance with test specific processing algorithms at step 243. The processed test measurement data is utilized to produce waveforms and corresponding appropriate reports at step 243. Server 109 downloads the reports and waveforms to the patient's Internet device at step 245. The patient may then view and store the reports and waveforms. The download to the patient is displayed on the patient's Internet device 245. The patient receives a graphical view of the test with comparisons to norms. A screen display of the information provided to the patient is shown in FIG. 11.

The processed data, reports and waveforms may be automatically routed to a preselected medical practitioner at a second Internet device 105. At step 247, server 109 determines if the patient has pre-authorized downloading the test results to another person. The other person can be a medical practitioner. If the patient has authorized such a download, server 109 automatically downloads the test results to the preselected authorized medical practitioner's Internet device 105 at step 249.

The system of the present invention may also be operated in a second mode in which test measurement data is made available in substantially real-time to server 109. In this second mode of operation, the Internet connection between Internet device 103 and server 109 is not dropped or is re-established after the patient has attached the sensors and a diagnostic program verifies operation of the sensors. Test measurement data is transmitted in substantially real-time from Internet device 103 to server 109. Server 109 processes the test measurement data and makes a test measurement data available to one or more authorized preselected medical practitioners. For example, a medical practitioner at Internet device 107 may be authorized by the patient to receive test measurement data in substantially real-time. In this second of operation and medical practitioner remotely located from the patient may monitor test measurement data in substantially real-time. This has certain advantages that are described in detail below.

In contrast to prior medical testing systems in which data is manually entered by a patient, in the present system, test measurement data is automatically obtained from the patient. The test measurement data is routed to a central site at which the data is analyzed and is automatically made available to medical personnel either in substantially real time or delayed until the medical personnel are available. Further in accordance with the invention, the medical personnel may be located anywhere that they have access to the Internet.

A database at the central source stores test information and patient facts. Test information retention is for a lifetime. The data has value to the individual and to the medical community as a source of information about cardiovascular health. The database is protected with security procedures.

At the central site, a database is utilized to store the test data and results for each patient. In addition, all prior test data and reports are stored in the database. By providing a centralized storage facility for medical test data, the patient as well as preselected medical practitioners may view the patient's history. In addition, trending algorithms are used to analyze present and past data to develop a medical condition trend that may be downloaded to the patient and/or his or her preselected medical practitioners.

Although the present embodiment of the invention contemplates that the Internet connection is dropped during the test set up and collection of test data, in other embodiments of the invention, the Internet connection may be maintained or may be reestablished as data collection occurs. The generation of resulting waveforms may be done in substantially real time thereby permitting monitoring of the patients condition either at the patient's personal computer or at any other location which may access the Internet and at which a preselected authorized medical practitioner is located. Advantageously, the permits substantially real time monitoring of a patent's condition anywhere in the world that access to the Internet is obtainable.

Test measurements made over time can be trended for each patient and reported as a track on heart health. In addition, patients who might otherwise have to be in a medical facility for connection to medical instrumentation may be allowed to be at home or other locations and still be able to be monitored by medical practitioners.

Still further, in accordance with one aspect of the invention, medication strategies can be documented and used to predict the affect of changes on other patients as developed by comparative analysis of historical medication strategies.

Operation of Web Site

Figure 3:
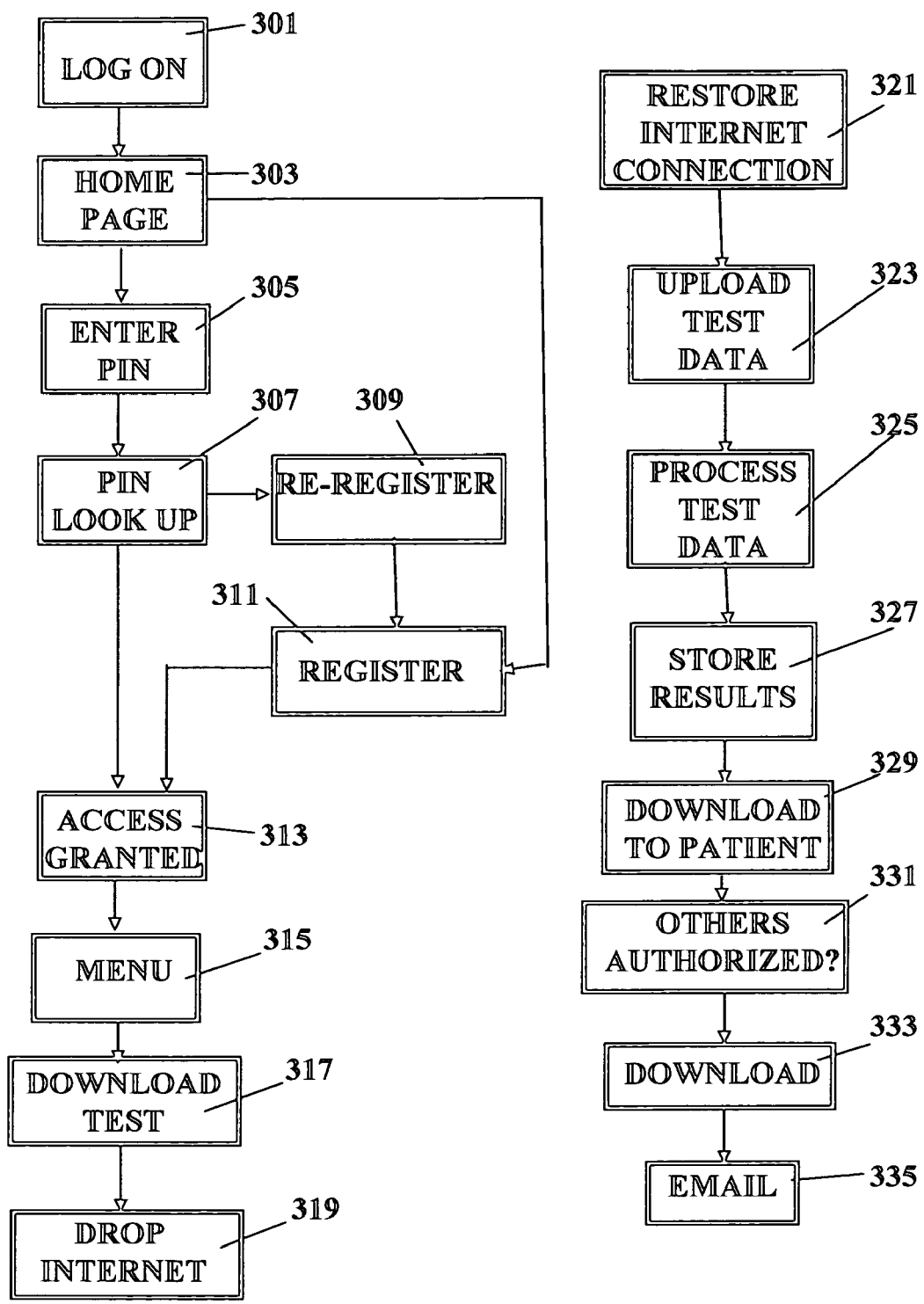
FIG. 3 is a flow diagram illustrating operation of the server shown in FIG. 1.

Turning now to FIG. 3, operation of server 109 is described in a flow diagram. Initially, server 109 receives a log on from a patient at step 301. Server 109 provides a home page that the patient may view at step 303. The patient, if a registered user provides his or her PIN number at step 305. Server 109 looks up the PIN number in a database at step 307 to verify that the patient has previously registered. If the PIN number is not found in the database or the registration of that PIN number has been suspended or canceled, the patient is denied access to records at step 307. The patient is provided with a message that he or she needs to re-register at step 309. If the patient was not previously registered or the PIN number is not valid, the patient is invited to register at step 311. Once the patient has completed registration at step 313 or if the patient has provided a valid PIN number, the central site allows the patient to have access to a menu screen at step 315.

If at the menu screen, the patient selects a test, server 109 downloads the appropriate testing program at step 317. In some instances, it may be desirable to maintain the Internet connection with the patient during the entirety of the testing process as noted above. If for example, a medical practitioner desires to have an Internet connection throughout the test process, the Internet connection may be maintained. However, in the present embodiment of the invention, after downloading the test programs the central site relinquishes the Internet connection to the patient at step 319.

After the test data has been obtained from the patient, an Internet connection is again established between patient Internet device 103 and the central site or server 109 at step 321. Test data is uploaded from the patient Internet device 103 to server 109 at step 323. Server 109 processes test measurement data to produce appropriate waveforms and reports at step 325. At step 327, the data, waveforms, and reports are stored in a database 550 for future reference. The waveforms and reports are downloaded to the patient Internet device 103 at step 329. In addition, server 109 obtains Internet addresses from its database of patient pre-authorized medical practitioners at step 331. Server 109 downloads patient waveforms and reports to a pre-authorized medical practitioner's Internet device 105 at step 333. The downloading to the pre-authorized medical practitioner Internet device 105 will occur substantially simultaneously with processing of the test measurement data if the medical practitioner has logged onto the web site as indicated at step 329. Otherwise, server 109, at step 335 generates an email to the medical practitioner to alert the medical practitioner that test information is available.

Medical Practitioner Operation

Figure 4:
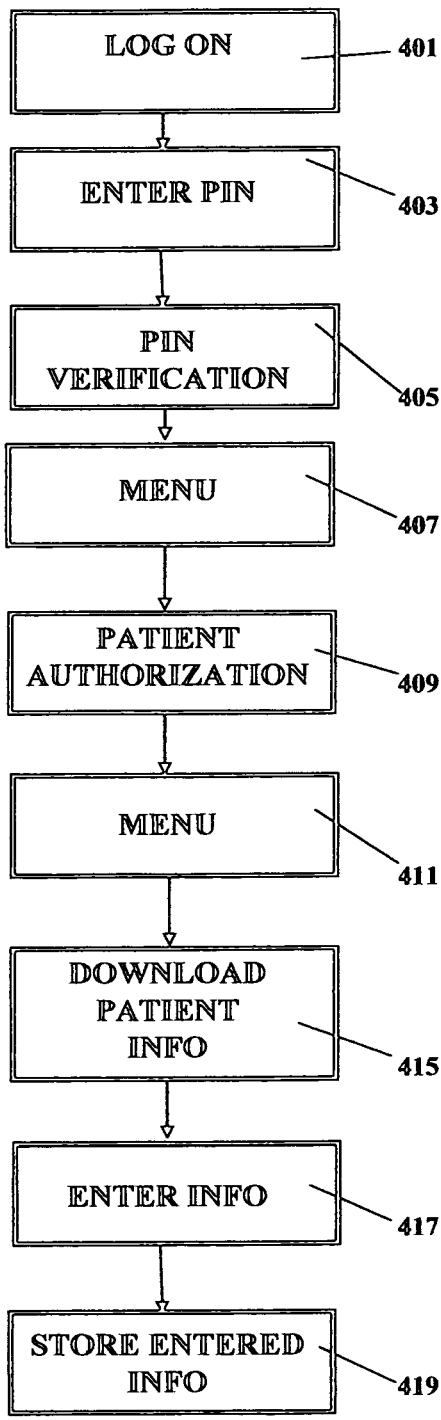
FIG. 4 is a flow diagram illustrating operation of the system of FIG. 1.

Turning now to FIG. 4, the use of the system and method of the invention is illustrated in a flow chart. A medical practitioner logs onto the web site of server 109 at step 401. The medical practitioner is presented with a screen at step 403 that permits him to register with the system for the first time, in which instance he or she will have to provide various registration information. The registration process utilized in the illustrative embodiment is one of several known registration processes. If the medical practitioner is already registered, the medical practitioner will provide a PIN and the PIN will be verified at step 405. After PIN verification, the medical practitioner is provided with a menu screen at step 407. If the medical practitioner desires to access the patient's test waveforms, records and related data, the medical practitioner enters his authorization code for the patient. Server 109 verifies that the medical practitioner is authorized to access that specific patient's records at step 409. The web site will provide another screen at step 411. From this screen, the medical practitioner may access recent or historical data for the patient. The patient information is downloaded to the medical practitioner's Internet device 105 at step 415. In addition, the medical practitioner may enter related information, such as prescriptions for drugs and the date at which the drug is prescribed. The medical practitioner information is entered at step 417 and stored by the system in a relational database at step 419.

System Server

Figure 5:
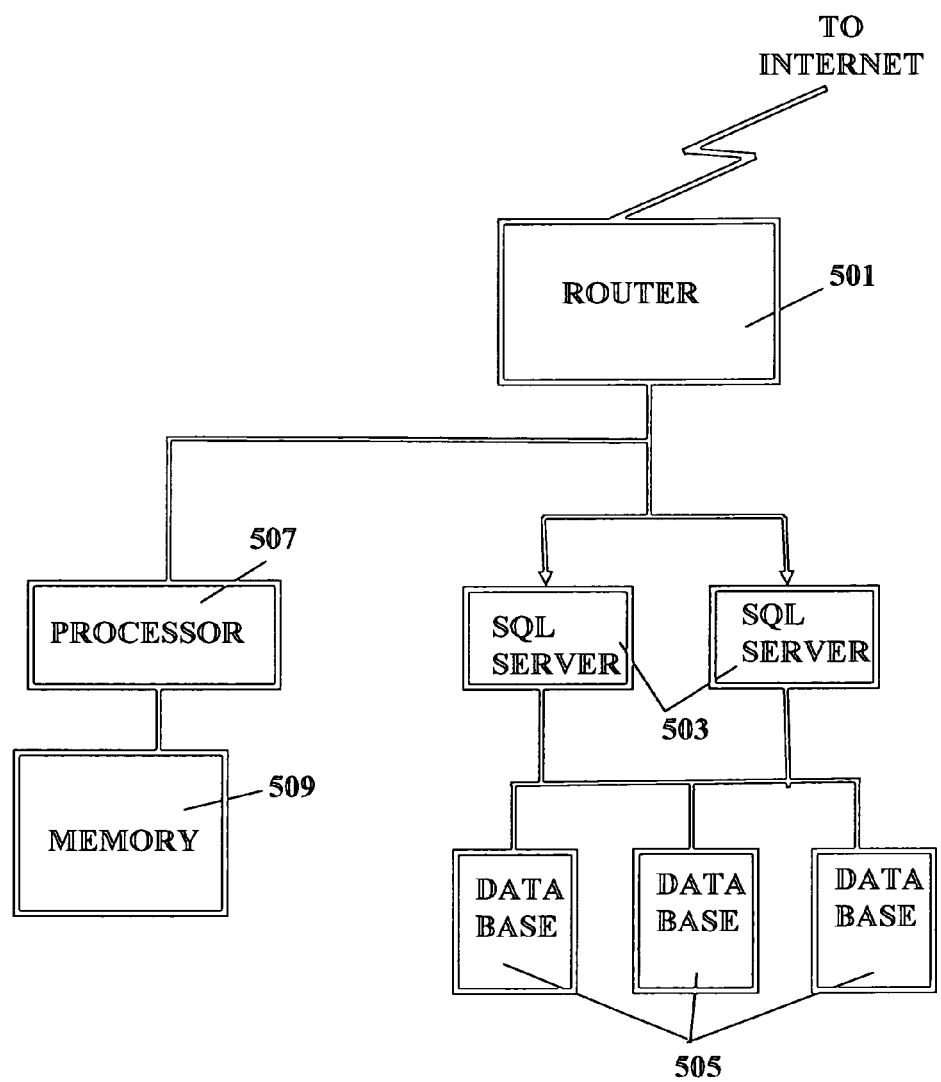
FIG. 5 is a block diagram of the server shown in FIG. 1.

A block diagram of a server 109 in accordance with the principles of the invention is shown in FIG. 5. Server 109 includes one or more processor units including routers 501, SQL or sequel servers 503, relational databases 505, processor units 507, and associated program memory 509. In operation, server 109 responds to site users by providing menu screens and responding to clicks from the users. The operation of the web site portion of server 109 with its various routers 501 and SQL or sequel servers 503 is substantially similar to the operation of known web site servers.

FIG. 6 is a flow diagram of the operation of server 109. Server 109 responds to a log on from an Internet device 103 at step 601 by providing a log-on screen. Part of a log-on screen requires that the patient provide his or her PIN number. Upon detecting that patient has clicked on the log-on screen at step 603, patient entered data is used to determine whether patient has previously registered or not. If the patient has not previously registered, server 109 provides a registration screen to the patient at step 605. If the patient entered a PIN number, server 109 verifies the validity of the PIN number by searching one or more of the databases 505 at step 607. Upon completion of registration or upon entry of a valid PIN number a menu screen is provided to the patient at step 609. If the patient selects a test on the menu screen, server 109 operates such that appropriate test software including training, testing, and diagnostic programs, are retrieved from databases 505 at step 611. The programs are downloaded to the patient Internet device 103 via Internet connection at step 613. Upon receipt of an acknowledgment from the patient's personal computer that the download has been successful at step 615, the Internet connection to the patient Internet device 103 is released. Server 109 will receive a request from the patient of Device 103 to process test measurement data at step 617. Server 109 will acknowledge the request of and initiate an uploaded of the data from the patient Internet device 103 at step 619. The uploaded test measurement data is processed by processor 507 in accordance with an appropriate algorithm retrieved from databases 505 at step 621. The algorithm is selected in accordance with the particular test has been performed.

Test measurement data is processed using the selected algorithm and converted into waveforms and reports at step 623 by processor 507. The waveforms and reports are stored at step 625 in the database 505 and associated with the particular patient. In addition, related test information such as the date and time of the test as well as pre-authorized medical practitioners and others who the patient desires to have access to the information are entered into the database at step 629. Processor 507 downloads the waveforms and reports to the patient Internet device 103 at step 631. In addition, where the patient has pre-authorized others to receive the waveforms and reports at step 633, processor 507 downloads waveforms and reports to those other individuals. In the event that one or more of the pre-authorized individuals is not presently logged onto the system, processor 507 retrieves an appropriate predetermine email message to data bases 505 and sends the mail message via the Internet to the one or more pre-authorized individuals.

In addition, processor 507 identifies requests to provide other information and causes SQL or sequel servers 503 to obtain such information from relational data bases 505. Still further, processor 507 responds to requests from patients and/or authorized medical practitioners and other authorized individuals to provide trending information. The system of invention includes computer programs stored in program memory 509 that may be used to generate trending information. When trending analysis is requested by a user or by a pre-authorized medical practitioner, a trending algorithm is loaded from memory 509 and is executed. Results of the trending are stored in relational database 505 so that a historical trending may be obtained. A relational database 505 is used to store other information related to test data that is stored in relational databases 505.

For example, prescription information may be entered and stored in the relational databases 505 such that it can be retrieved in conjunction with patient data. Prescription information includes time information so that the time relationship may be obtained relative to the prescription and test results. In some applications a patient may be requested to conduct tests several times in a day to determine what effect, if any, the prescription has upon test data. In one application of invention, new drug testing may utilize the system of invention such that instantaneous gathering of information from a large number of patients may be gathered on a real-time basis. It is believed that this application of the invention can speed the time to market of new drugs.

Cardiac Testing

The illustrative embodiment of invention is directed to cardiac healthcare and testing. Test of embodiment of invention utilizes impedance cardiography, database storage, computational techniques, and Internet to communications to compile and distribute information on cardiovascular health.

Impedance cardiography has been used in stand-alone devices and various medical surroundings. The impedance cardiography test utilized in the system of the invention collects 19 hemodynamic measurements. The measurements are equivalent to the data collected from a right heart catheterization procedure. Right heart catheterization is a dangerous, invasive, and expensive procedure. In contrast, impedance cardiography is not dangerous, not invasive, and inexpensive.

Four key measurements provide a comprehensive profile of hemodynamic function. These four key measurements include cardiac output, left ventricular ejection time, thoracic fluidity, and total systemic resistance. Cardiac output is the quantity of blood ejected in one cardiac cycle. Left ventricular ejection time is the time from aortic valve opening to closure during the systolic portion of the cardiac cycle. Thoracic fluidity is the amount of water in the thorax; excess fluid results in congestive heart failure. Total systemic resistance is the resistance value for the systemic circulation; and is a measure of the amount of "clogging" in the arteries. The measurements are taken in two positions, supine and standing. Comparison of heart function in the two positions provides additional information about hemodynamic function. In certain instances, and in particular for certain applications of impedance cardiography, a program is executed that utilizes equivalencies to normalize the impedance cardiography test measurements to right heart catheterization by performing impedance cardiography testing before and after a catheterization. The normalized results eliminate needs for future use of the invasive catheterization procedure.

In the illustrative embodiment of invention, preparation for test occurs through the Internet web site maintained by server 109. Impedance sensors are utilized to collect test data. The impedance sensors are shipped to the patient in advance of the testing. Alternatively, medical practitioners or drugstores can distribute the impedance sensors. When the patient has the impedance sensors, the patient logs onto the web site provided by server 109 described herein above. The test program is downloaded from server 109 to the patient's Internet device 103 for execution of testing. The program in the device 103 directs the procedure, collects data from impedance sensors, conditions the data, and transmits the data to server 109.

Figure 7:
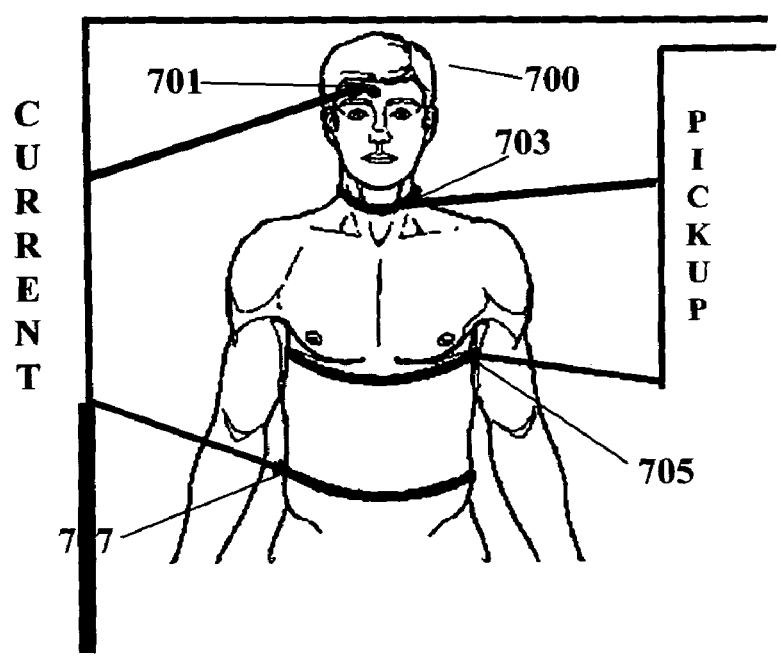
FIG. 7 illustrates attachment of sensors to a patient.

Turning now to FIG. 7, four impedance sensors 701, 703, 705, 707 are attached to the patient 700. Impedance sensor 701 is attached to the patient's forehead. Impedance sensor 703 is attached to the patient's throat. Impedance sensor 705 is attached to the patient's chest. Impedance sensor 707 is attached to the patient's abdomen. Leads from each of the sensors 701, 703, 705, 707 attach to patient's Internet device 103. The patient's Internet device 103 comprises a personal computer. Sensors 701, 703, 705, 707 are easy to attach and require no special training. Internet device 103 plays in multimedia instructional program instructing the patient on the attachment of each of the sensors 701, 703, 705, 707. As described above, yet device 103 runs a diagnostic program to check the sensors. After the sensors have been checked, the test program runs.

The instructional program instructs the patient to first lay down, i.e., to assume a first testing position. When the patient is in the first testing position, the patient provides an indication readable by the program that he or she is in the first testing position. Internet device 103 takes measurements from the sensors 701, 703, 705, 707. Measurements are taken twice while the patient is in a lying down (supine) position. The program instructs the patient when testing in the first position is complete. The program then instructs the patient to assume a second testing position, i.e., sitting or standing. When the patient is in the second position, the patient provides an indication to the program that he or she is in position. Measurements are taken twice with the patient in the second position. Having the patient switch from lying to standing maximizes the volumetric shift. The duration of each of the four test measurements requires 25 heartbeats or about 30 seconds to complete.

An Internet connection is established between the patient's Internet device 103 and server 109. Test measurement data is uploaded to server 109. A secured capsule is utilized for transmission to server 109. Server 109 receives and decodes the encrypted data. Server 109 completes processing of the test data to produce impedance cardiography waveforms and generates reports. Server 109 downloads the waveforms and reports to the patient's Internet device 103 for viewing. Server 109 stores the data in databases 505 shown in FIG. 5 for reference and analysis. In addition, as described above, the waveforms, report, and data may be routed to a pre-authorized medical practitioner at another Internet device 105. Databases 505 store tests and patient's facts.

A clear advantage of the present invention is that by utilizing the Internet, border and time dependencies are eliminated. Doctor and patient can be linked from anywhere in the world. The best cardiologists can be employed where needed. A patient in London and a doctor in Los Angeles can "tune" a pacemaker. Effects of medication can be monitored and altered with the patient at home or at other locations remote from the site of the medical practitioner. A system in accordance with the invention merges medical and information technologies at levels never before contemplated to produce a detailed, comprehensive lifetime cardiovascular health history available anywhere at anytime for anyone as authorized by the patient.

By maintaining the patient's cardiovascular measurements in a database that is accessible any time from virtually anywhere, the patient is by virtue of the instant accessibility likely to maintain a testing regimen. The ability of the system to compare test measurement results of multiple impedance cardiography tests encourages repeated tests. Heart disease patients will utilize these capabilities to monitor their health on a regular basis. The same capabilities will provide physicians with the informational insight to anticipate crisis, regulate pacemakers, and manage medication.

Figure 8:
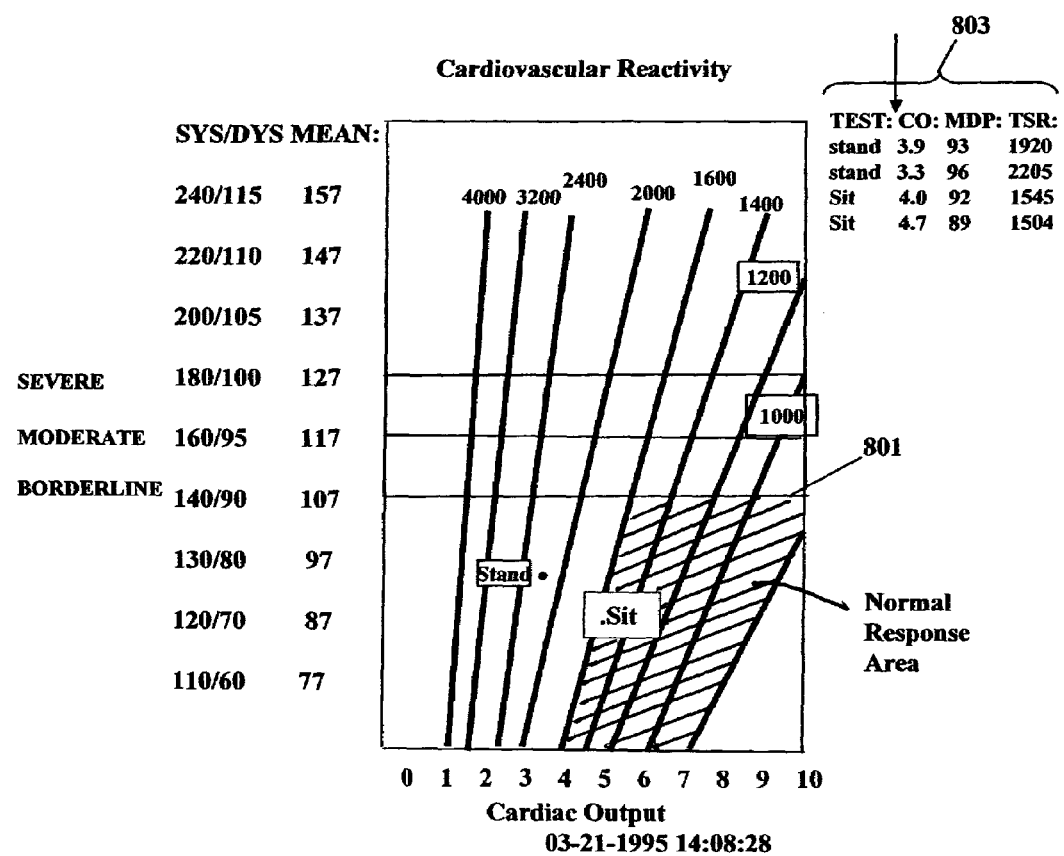
FIG. 8 is a chart of test measurement data.

FIG. 8 charts three key measurements, i.e., pressure, reactivity, and cardiac output from the test measurement data and illustrates the relative cardiovascular reactivity to emotional stress. The relationship of the measured cardiovascular performance to standardized emotional stressors is determined by plotting three variables and highlighting a normal area 801 for a quick understanding of vardiovascular health. The upper right hand corner 803 contains the raw plot data for the four tests "CO" is cardiac output in liters (the amount of blood pumped by the heart). "MBP" is the mean blood pressure, an averaging of the two blood pressure measures (systolic and diastolic). "TSR" is Total Systemic Resistance to blood flow. TSR is a gauge of the resistance in the blood vessels to the flow of blood (clogged artery measurement). Summarization of this data into a single graphic provides an assessment of heart health. These variables represent three of 19 measurements produced by the impedance cardiography system of the invention.

Periodic testing in conjunction with entry of other patient specific information will provide trend analysis that will highlight changes in cardiovascular health. For example, the effect of exercise, weight change, and diet will be reflected in these measurements.

FIG. 9 is a screen display of detailed measurement values in a medical practitioners review form. This data is supplemented with a resource library stored in relational database 505 and accessible via server 109 to explain the information and advise physicians on treatments.

Use of a system in accordance with the invention is particularly advantageous to individual medical practitioners, visiting nurses and pediatric specialists. The physician can prescribe utilizing the system of the invention at the office or in the home at intervals determined by the need for information about the heart. This capability is lacking in today's treatments.

Figure 10:
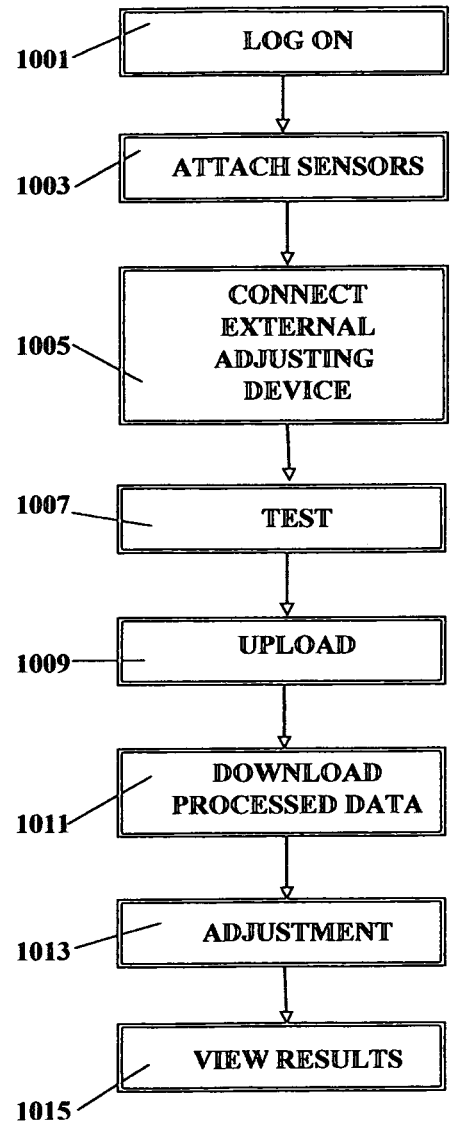
FIG. 10 is a flow diagram illustrating remote adjustment of an implanted device.

The present invention permits remote monitoring of cardiac conditions of patients. There are specific instances in which this remote monitoring capability is particularly significant. In particular, a cardiac specialist can utilize the system and method of the illustrative embodiment to remotely adjust or tune a pacemaker. FIG. 10 illustrates a method of utilizing the system of the invention to remotely adjust a pacemaker. Pacemaker and other cardiac devices are known in which the device may be implanted and yet are externally adjusted. Typically an adjusting device is placed proximate the implanted device and external to the patient. Wireless coupling between the implanted and external device is used to permit adjustment of the implanted device. In the method shown in the flow diagram of FIG. 10, a patient may have an external adjustment device. The patient utilizing an Internet device 103 logs onto server 109 at step 1001. Typically, the patient's cardiologist also logs onto server 109 via Internet device 105. The patient attaches sensors 701, 703, 705, 707 and connects the sensors to the Internet device at step 1003. The patient connects the external adjusting device to Internet device at step 1005. Test measurement data is taken at step 1007 and uploaded to server 109 at step 1009. Server 109 processed the test measurement data and downloads it to the cardiologist at step 1011. The cardiologist in turn adjusts the implanted device via the Internet connection at step 1013. Test measurements are performed during the entirety of the period in which the cardiologist is adjusting the implanted device such that the cardiologist can have automatic and substantially instantaneous feedback as to the results of the adjustment. The cardiologist views the results of the adjustment at step 1015 and either further adjusts the implanted device or is satisfied with the adjustment and terminates the process by logging off server 109. During the adjustment, data continues to be stored in relational database 550 to provide a history of all activity for the patient.

Other implanted pacemakers have been designed to be externally adjustable with an external device by the patient. Just as a medical practitioner can use the system and method of the invention to adjust the implanted device, a patient is better able to adjust his or her own device by viewing the effects of the adjustment on his or her test measurements utilizing. In this instance, the patient can self monitor the effect of the adjustment by for example running the cardiac tests, making an adjustment to his or her implanted device and viewing the effects by running the test again immediately after the adjustment. This arrangement results in better and more useful adjustments. By utilizing a wireless Internet device, the patient can make the adjustment while engaged in normal daily activities or located in remote locations.

The primary purpose of medication for heart patients is to produce an acceptable level of cardiovascular performance as measured. The parameters measured by the system in accordance with the invention provide information from which a physician can evaluate and regulate medication. Regular check pointing of medication effectiveness can provide insight the doctor needs to provide the best mix. Home use of a system in accordance with the invention saves time and is time independent allowing for more dependable use of the procedure.

In one application of the system of the invention, patient performance is measured for a diet and exercise regimen prescribed by the physician. The system of the invention stores all test information for a patient in relational databases 550. The historical data is used to produce a "report card"—proof of the success or failure of the plan. The regular feedback and increased understanding of the goals and their relationship to system obtained data will be the basis for motivation and improved health management. Physician-prescribed plans of treatment record expected results into a patient profile for comparison to results recorded by the system test results. The visibility of progress (or regression) becomes a motivational instrument.

Regular monitoring can alert the treating physician when hemodynamic measurements deteriorate prior to occurrence of crisis.

Individuals concerned about their cardiovascular health, such as athletes and hypochondriacs, can employ the system of the invention to provide comparative data for their age and sex. Athletes could measure the training effectiveness in cardiac output and resistance to blood flows. Others could compare statistics with control groups.

The invention has been described in conjunction with specific embodiments. It will be appreciated by those skilled in the art that various changes and modifications may be made to the various embodiments without departing from the spirit or scope of the invention. It is intended that those various changes and modifications be included within the scope of the invention. It is further intended that the invention not be limited to the various embodiments shown and described herein nor limited to those embodiments that would be apparent as of the filing date of this application. It is intended that the invention be limited in scope only by the claims appended hereto.

It is further intended that the uses of means plus function language not limit the invention to particular structures shown and described in this disclosure or to equivalent structures. It is intended that structural equivalents, equivalent structures as well as the particular structures shown and described are included in the scope of the claimed invention.

What is claimed is:

1. A method of providing medical testing comprising:
providing central serving apparatus coupled to the Internet;
utilizing said central serving apparatus to access impedance cardiography test measurement software;
utilizing said central serving apparatus to access one or more computer program impedance cardiography algorithms for processing impedance cardiography test measurement data;
operating said central serving apparatus to download said impedance cardiography test measurement software, via the Internet, to patient Internet apparatus;
utilizing said downloaded impedance cardiography test measurement software at said patient Internet device to provide sensor placement information of impedance sensors to a patient;
utilizing said impedance cardiography test software at said patient Internet device to provide diagnostic testing operation and operability of said impedance sensors;
obtaining medical test measurement data via said impedance sensors;
uploading said impedance cardiography test measurement data to said central server from remote locations via said patient Internet apparatus via the Internet;
selecting one computer program impedance cardiography algorithm from said at least one or more computer program impedance cardiography algorithms at said central serving apparatus;
utilizing said one computer program impedance cardiography algorithm at said central serving apparatus to process said impedance cardiography test measurement data;
processing said impedance cardiography test measurement data in accordance with said one computer program impedance cardiography algorithm to produce test information from said impedance cardiography test measurement data; and
downloading said test information to predetermined user apparatus coupled to the Internet.

2. A method in accordance with claim 1, comprising:
providing a data base accessible by said central serving apparatus; and
storing said test information in said database.

3. A method in accordance with claim 1, comprising:
receiving patient identification information for said test measurement data;
storing said test information in a database; and
associating said stored test information with said patient identification information.

4. A method in accordance with claim 3, comprising:
receiving a request for said test information from a requester; and
determining that said requester has authorization to obtain said test information.

5. A method in accordance with claim 4, comprising:
receiving said request via the Internet.

6. A method in accordance with claim 4, comprising:
downloading said requested test information to said requester via the Internet.

7. A method in accordance with claim 3, comprising:
receiving a request for said test information from a requester that has no authorization to obtain information;
determining that said requester has no authorization; and
rejecting said request.

8. A method in accordance with claim 1, comprising:
receiving a request via the Internet for testing from patient Internet apparatus; and
downloading via the Internet said impedance cardiography test measurement software to said subject Internet apparatus.

9. A method in accordance with claim 8, comprising:
storing said impedance cardiography test measurement software in memory located proximate said central server.

10. A method in accordance with claim 8, comprising:
downloading automatic un-install software with said impedance cardiography test measurement software, said automatic un-install software being automatically operable to un-install said impedance cardiography test measurement software upon successful uploading of said impedance cardiography test measurement data to said central serving apparatus.

11. A method in accordance with claim 10, comprising:
automatically un-installing said impedance cardiography test measurement software after uploading said test measurement data.

12. A method in accordance with claim 8, comprising:
automatically un-installing said impedance cardiography test measurement software after uploading said impedance cardiography test measurement data.

13. A method in accordance with claim 1, comprising:
receiving a request via the Internet for testing from patient Internet apparatus; and
downloading impedance cardiography testing information to said patient Internet apparatus.

14. A method in accordance with claim 13, comprising:
storing said impedance cardiography testing information proximate said central server.

15. A method in accordance with claim 13, comprising:
providing said impedance cardiography testing information as multimedia information displayable at said patient Internet apparatus.

16. A method in accordance with claim 1, wherein:
said impedance cardiography test measurement software includes a multimedia presentation that steps a patient through positioning and attachment of at least one impedance cardiography sensor.

17. A method in accordance with claim 16, wherein:
said impedance cardiography test measurement software responds to said diagnostic testing indicating improper impedance cardiography sensor operation by directing the patient through a corrective routine.

18. A method in accordance with claim 1, comprising:
executing a verification routine to determine that said impedance cardiography test measurement data appears to be valid data.

19. A method in accordance with claim 3, comprising:
receiving information for authorized access of said impedance cardiography test information from the individual identified by said patient identification information.

* * * * *